US012770266B2

(12) United States Patent
Li et al.

(10) Patent No.: US 12,770,266 B2
(45) Date of Patent: Oct. 20, 2026

(54) SINGLE VERTEBRA SEGMENTATION METHOD, DEVICE, EQUIPMENT AND STORAGE MEDIUM

(71) Applicant: TINAVI MEDICAL TECHNOLOGIES CO., LTD., Beijing (CN)

(72) Inventors: Chunlin Li, Beijing (CN); Tiechang Liu, Beijing (CN); Cheng Zhu, Beijing (CN)

(73) Assignee: TINAVI MEDICAL TECHNOLOGIES CO., LTD., Beijing (CN)

( * ) Notice: Subject to any disclaimer, the term of this patent is extended or adjusted under 35 U.S.C. 154(b) by 223 days.

(21) Appl. No.: 18/751,211

(22) Filed: Jun. 22, 2024

(65) Prior Publication Data

US 2024/0420337 A1 Dec. 19, 2024

Related U.S. Application Data

(63) Continuation of application No. PCT/CN2023/137405, filed on Dec. 8, 2023.

(30) Foreign Application Priority Data

Jun. 15, 2023 (CN) ......................... 202310714385.7

(51) Int. Cl.
*G06T 7/12* (2017.01)
*A61B 6/00* (2006.01)
(Continued)

(52) U.S. Cl.
CPC .............. *G06T 7/12* (2017.01); *A61B 6/5205* (2013.01); *G06T 5/10* (2013.01); *G06T 7/155* (2017.01);
(Continued)

(58) Field of Classification Search
CPC .. G06T 7/12; G06T 5/10; G06T 7/155; G06T 7/73; G06T 2207/10081;
(Continued)

(56) References Cited

U.S. PATENT DOCUMENTS

2008/0044074 A1 2/2008 Jerebko
2011/0040168 A1 * 2/2011 Arnaud ................ G06T 7/0012 600/407

(Continued)

FOREIGN PATENT DOCUMENTS

CN 108230301 A 6/2018
CN 110599508 A 12/2019

(Continued)

OTHER PUBLICATIONS

Sekuboyina A., Husseini M.E., Bayat A., Löffler M., Liebl H., Li H., Tetteh G., Kukačka J., Payer C., Štern D., et al. Verse: A vertebrae labelling and segmentation benchmark for multi-detector CT images Med. Image Anal., 73 (2021), Article 102166 (Year: 2021).*

(Continued)

*Primary Examiner* — Ian L Lemieux
*Assistant Examiner* — Noah William Boyar
(74) *Attorney, Agent, or Firm* — JEEN IP LAW, LLC

(57) ABSTRACT

A single vertebra segmentation method, device, equipment and storage medium. The method comprises: acquiring first spine boundary information, which is boundary information of a spine in a segmentation result obtained through image segmentation of a raw CT image; acquiring first vertebra position information, which is information on the position of a single vertebra in the spine in the raw CT image; acquiring an initial image of the single vertebra according to the first spine boundary information and the first vertebra position information; marking the position of the single vertebra in the initial image of the single vertebra to generate an updated (Continued)

image of the single vertebra; and determining the single vertebra in a restored image corresponding to the raw CT image according to the updated image of the single vertebra. According to the present application, the spine in the CT image can be segmented on a single segment basis.

6 Claims, 12 Drawing Sheets

(51) Int. Cl.
*G06T 5/10* (2006.01)
*G06T 7/155* (2017.01)
*G06T 7/73* (2017.01)

(52) U.S. Cl.
CPC ...... *G06T 7/73* (2017.01); *G06T 2207/10081* (2013.01); *G06T 2207/20036* (2013.01); *G06T 2207/20048* (2013.01); *G06T 2207/20084* (2013.01); *G06T 2207/30012* (2013.01); *G06T 2207/30204* (2013.01)

(58) Field of Classification Search
CPC . G06T 2207/20036; G06T 2207/20048; G06T 2207/20084; G06T 2207/30012; G06T 2207/30204; G06T 7/11; A61B 6/5205
See application file for complete search history.

(56) References Cited

U.S. PATENT DOCUMENTS

2020/0245960 A1* 8/2020 Richter .................. A61B 6/032
2021/0334975 A1* 10/2021 Yang ...................... G06N 3/084
2021/0335480 A1* 10/2021 Johnsson ............... G06N 3/045
2021/0343003 A1* 11/2021 Koenig .................. A61B 34/10
2021/0374452 A1* 12/2021 Chen ....................... G06N 3/045
2022/0180521 A1* 6/2022 Wu ........................ G06V 10/26
2022/0207722 A1* 6/2022 Kim ...................... G06T 7/0012
2022/0237779 A1* 7/2022 Rajapakse ............ A61B 6/5217
2022/0375091 A1* 11/2022 Sun ...................... G06V 10/809
2023/0005138 A1* 1/2023 Kuang .................. G06T 3/4007
2023/0289967 A1* 9/2023 Jalal ...................... G06T 7/0012
2023/0410985 A1* 12/2023 Brynolfsson ......... G06T 7/0012
2024/0153644 A1* 5/2024 Crawford ............... G16H 50/20
2024/0177836 A1* 5/2024 Paik ....................... A61B 5/742
2025/0200746 A1* 6/2025 Lossau .................. G06T 7/0012

FOREIGN PATENT DOCUMENTS

CN 113643314 A 11/2021
CN 114998297 A 9/2022
CN 115439453 A 12/2022
CN 116563218 A 8/2023
CN 116862933 A 10/2023
GB 2559013 A * 7/2018 ............. G06V 10/50

OTHER PUBLICATIONS

Zhou, Zhengyin, Fu, Zhihui, Jia, Juncheng, Lv, Jun, Rib Fracture Detection with Dual-Attention Enhanced U-Net, Computational and Mathematical Methods in Medicine, 2022, 8945423, 13 pages, 2022. (Year: 2022).*

* cited by examiner

SINGLE VERTEBRA SEGMENTATION METHOD, DEVICE, EQUIPMENT AND STORAGE MEDIUM

CROSS-REFERENCE TO RELATED APPLICATIONS

This application is a continuation of co-pending International Patent Application No. PCT/CN2023/137405, filed on Dec. 8, 2023, which claims the priority and benefit of Chinese patent application number 202310714385.7, filed on Jun. 15, 2022 with China National Intellectual Property Administration, the entire contents of which are incorporated herein by reference.

TECHNICAL FIELD

The present application relates to the technical field of medical image processing, in particular to a single vertebra segmentation method, a single vertebra segmentation device, a single vertebra segmentation equipment and a storage medium.

BACKGROUND

Presently, a spinal surgeon usually must make a surgical plan according to CT image data of a patient before an operation. The surgeon needs clearer and more intuitive CT images of the spine to make an accurate diagnosis. Therefore, it is of great significance to segment the CT images of the spines at a high precision on a single segment basis in spine surgery.

The inventor of the present application has found that it is easier to segment the spine on a single segment basis than to separate the spine entirely from the background information. However, the similarity of adjacent structures of the spine in strength and the differences between the vertebrae in different parts of the spine in shape and size increase the difficulty in single-segment segmentation of the spine.

SUMMARY

According to an aspect of the present application, there is provided a single vertebra segmentation method, which comprises the following steps: acquiring first spine boundary information, which is boundary information of a spine in a segmentation result obtained through image segmentation of a raw CT image; acquiring first vertebra position information, which is information on the position of a single vertebra in the spine in the raw CT image; acquiring an initial image of the single vertebra according to the first spine boundary information and the first vertebra position information; marking the position of the single vertebra in the initial image of the single vertebra to generate an updated image of the single vertebra; and determining the single vertebra in a restored image corresponding to the raw CT image according to the updated image of the single vertebra.

According to some embodiments, acquiring first spine boundary information comprises: constructing a first network model; acquiring a segmentation result of spine, sacra and ribs in the raw CT image by means of the first network model to obtain a segmented image of the raw CT image; performing morphological expansion on the spine in the segmented image to obtain a morphologically expanded spine image; transforming the morphologically expanded spine image into a first spine image in an image coordinate system; and acquiring the first spine boundary information corresponding to the first spine image.

According to some embodiments, acquiring first vertebra position information comprises: constructing a second network model; and acquiring the first vertebra position information from the raw CT image by means of the second network model.

According to some embodiments, acquiring an initial image of the single vertebra according to the first spine boundary information and the first vertebra position information comprises: determining boundary information of the single vertebra according to the first spine boundary information and the first vertebra position information; and acquiring the initial image of the single vertebra from the first spine image according to the boundary information of the single vertebra.

According to some embodiments, marking the position of the single vertebra in the initial image of the single vertebra to generate an updated image of the single vertebra comprises: determining second spine boundary information, which is spine boundary information in the initial image of the single vertebra; updating the position information of the single vertebra in the initial image of the single vertebra according to the second spine boundary information; acquiring a position marker of the single vertebra in the initial image of the single vertebra according to the updated position information of the single vertebra; transforming the initial image of the single vertebra containing the position marker of the single vertebra into a position marker image of the single vertebra in a body coordinate system; and generating the updated image of the single vertebra according to the initial image of the single vertebra and the position marker image of the single vertebra.

According to some embodiments, generating the updated image of the single vertebra according to the initial image of the single vertebra and the position marker image of the single vertebra comprises: constructing a third network model; transforming the initial image of the single vertebra into an initial image of the single vertebra in the body coordinate system; inputting the initial image of the single vertebra in the body coordinate system and the position marker image of the single vertebra into the third network model in a preset order; acquiring an updated image of the single vertebra in the preset order by means of the third network model; and transforming the updated image of the single vertebra into an updated image of the single vertebra in an image coordinate system.

According to some embodiments, determining the single vertebra in a restored image corresponding to the raw CT image according to the updated image of the single vertebra comprises: transforming the raw CT image into a raw image in the image coordinate system; acquiring a zero-pixel image corresponding to the raw image; marking the single vertebra in the zero-pixel image in the preset order according to the updated image of the single vertebra in the image coordinate system; acquiring a position marker of the single vertebra in the raw image according to the zero-pixel image corresponding to the raw image of the marked single vertebra; updating single vertebra boundary information in the raw image of the marked single vertebra according to the updated image of the single vertebra in the image coordinate system to determine the single vertebra in the raw image; and taking the raw image of the determined single vertebra as the restored image.

According to an aspect of the present application, there is provided a single vertebra segmentation device, which comprises: a data acquisition module for acquiring a raw CT image; a data processing module for setting a first network model, a second network model and a third network model; acquiring a segmentation result of spine, sacra and ribs from the raw CT image by means of the first network model; acquiring first spine boundary information according to the segmentation result; acquiring first vertebra position information from the raw CT image by means of the second network model; acquiring an initial image of the single vertebra according to the first spine boundary information and the first vertebra position information; marking the position of the single vertebra in the initial image of the single vertebra; generating an updated image of the single vertebra by means of the third network model according to the initial image of the single vertebra and a position marker image of the single vertebra; and determining the single vertebra in a restored image in an image coordinate system corresponding to the raw CT image according to the updated image of the single vertebra; and a data output module for outputting the restored image after the single vertebra is determined.

According to an aspect of the present application, there is provided an electronic device, which comprises: one or more processors; a storage device for storing one or more programs, which, when executed by the one or more processors, instruct the one or more processors to implement the afore-mentioned method.

According to an aspect of the present application, there is provided a computer-readable storage medium, on which a computer program or instructions are stored, which, when executed by a processor, implement the afore-mentioned method.

According to the embodiments of the present application, the spine in the CT image can be segmented by means of neural network models, and the CT image can be divided into small images corresponding to individual vertebrae arranged sequentially, thereby the problem that it is difficult to perform single-segment segmentation of the spine in the prior art is solved, the time of spine segmentation is shortened, the accuracy of spine segmentation is improved, and the spine segmentation is more efficient and faster.

It should be understood that both the above general description and the following detailed description are exemplary only, and are not intended to limit the present application.

BRIEF DESCRIPTION OF DRAWINGS

To explain the technical scheme in the embodiments of the present application more clearly, the drawings to be used in the description of the embodiments will be introduced briefly below. Obviously, the drawings in the following description only illustrate some embodiments of the present application.

DESCRIPTION OF EMBODIMENTS

Figure 1:
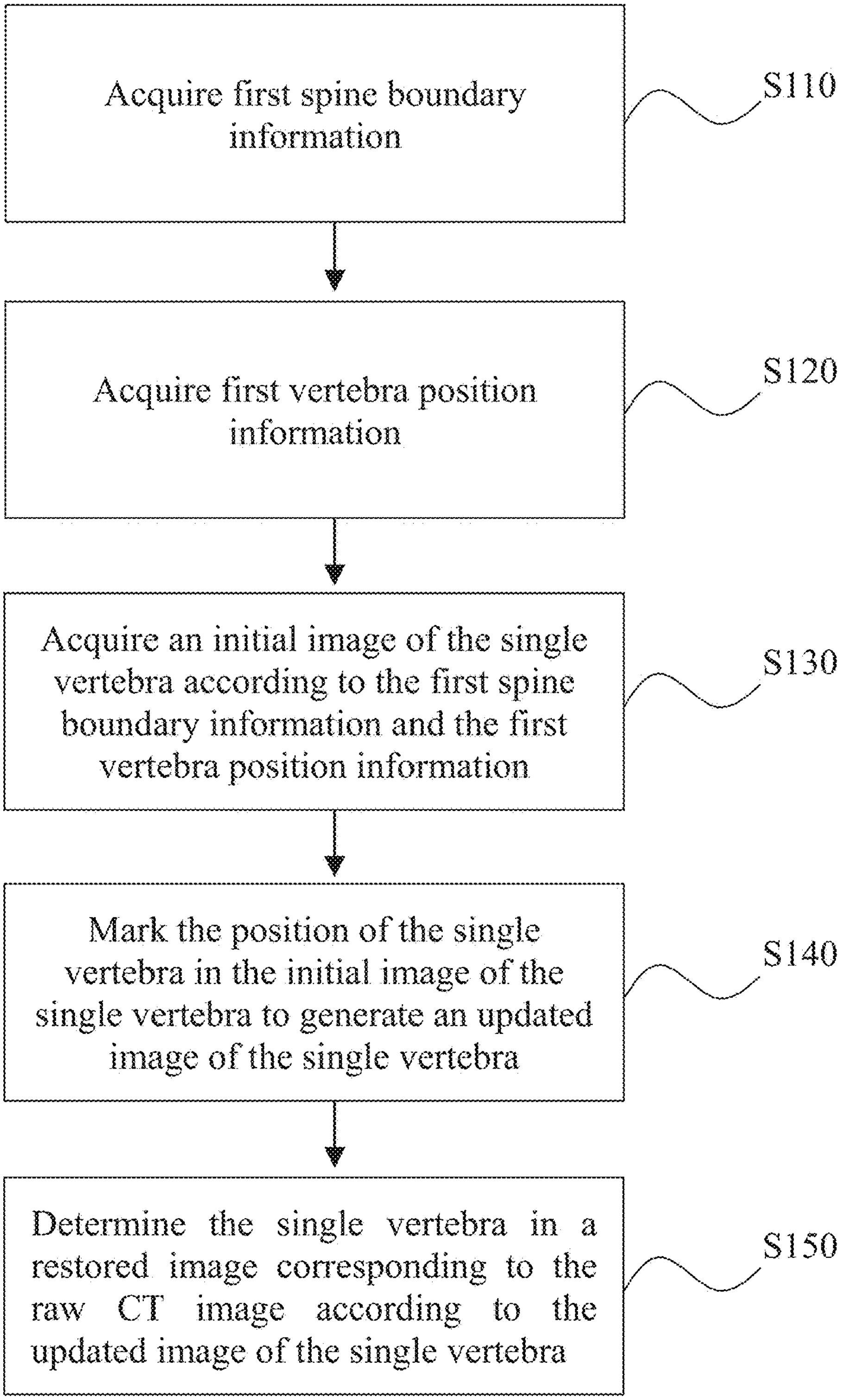
FIG. 1 shows a flowchart of a single vertebra segmentation method according to an example embodiment of the present application.

Now, example embodiments will be described more thoroughly with reference to the accompanying drawings. However, the example embodiments may be implemented in various forms and should not be construed as limited to the embodiments set forth herein; rather, these embodiments are provided to explain the present application thoroughly and completely, and fully convey the inventive concept of the example embodiments to those skilled in the art. In the drawings, the same or similar parts are represented by the same reference numerals, therefore repeated descriptions thereof will be omitted.

The features, structures, or characteristics described herein may be combined in any suitable manner in one or more embodiments. In the following description, numerous specific details are provided to give a thorough understanding on the embodiments of the present application. However, those skilled in the art can readily appreciate that the technical scheme of the present application can be practiced without one or more of those specific details, or in other ways, or with other components, materials, devices or operations. In these cases, well-known structures, methods, devices, implementations, materials or operations will not be shown or described in detail.

The flowcharts shown in the drawings are only illustrative, and do not necessarily include all contents and operations/steps, nor do they have to be executed in the described order. For example, some operations/steps can be split, while others can be combined or partially combined. Therefore, the actual order of execution may vary according to the actual situation.

The terms "first", "second" and the like in the description, claims and accompanying drawings of the present application are intended to distinguish different objects, rather than to describe a specific order of the objects. In addition, the terms "comprise", "include" and "have" and any variants thereof are intended to cover non-exclusive inclusion. For example, a process, method, system, product or apparatus including a series of steps or units is not limited to the listed steps or units, but optionally further includes steps or units that are not listed, or optionally further includes other steps or units inherent to the process, method, product or apparatus.

The present application provides a single vertebra segmentation method, a single vertebra segmentation device, a single vertebra segmentation equipment and a storage medium, which can realize fast and effective single-segment segmentation of a spine by means of neural network models and improve the accuracy of the single-segment segmentation.

The single vertebra segmentation method, single vertebra segmentation device, single vertebra segmentation equipment and storage medium according to embodiments of the present application will be described in detail below with reference to the accompanying drawings.

The present application involves the following term:

Zero-pixel image: an image obtained by replacing all the elements in a three-dimensional matrix corresponding to the coordinates of the points in an image coordinate system with 0. The pixel tag value of each point in the zero-pixel image is 0.

FIG. 1 shows a flowchart of a single vertebra segmentation method according to an example embodiment of the present application.

As shown in FIG. 1, in step S110, first spine boundary information is acquired.

For example, in step S110, the first spine boundary information is acquired by means of a first network model, wherein the first spine boundary information is boundary information of a morphologically expanded spine in a raw CT image.

In a specific embodiment of the present application, the specific steps of obtaining the first spine boundary information are as follows:

A first network model is constructed, and the raw CT image is inputted into the first network model, so as to obtain a segmentation result of spine, sacra and ribs in the raw CT image by means of the first network model, thereby obtain a segmented image of the raw CT image.

After the segmentation result is obtained, in order to avoid an incomplete or inaccurate spine boundary, morphological expansion is performed on the spine in the segmented image, thereby a morphologically expanded spine image is obtained.

The morphologically expanded spine image in a body coordinate system is transformed into a first spine image in an image coordinate system.

Corresponding morphologically expanded spine boundary information, i.e., the first spine boundary information, is obtained according to the first spine image.

According to some embodiments, the first spine boundary information includes left and right boundaries of the morphologically expanded spine image in a direction from the transverse process on one side of the vertebra to the transverse process on the other side of the vertebra (X-axis), front and back boundaries in a direction from the spinous process of the spine to the vertebral body (Y-axis), and upper and lower boundaries in a direction from sacral vertebrae to cervical vertebrae (Z-axis).

In step S120, first vertebra position information is acquired.

For example, in step S120, the first vertebra position information is acquired by means of a second network model, wherein the first vertebra position information is position information of the single vertebra in the spine in the raw CT image.

In a specific embodiment of the present application, the specific steps of obtaining the first vertebra position information are as follows:

A second network model is constructed, and the raw CT image is inputted into the second network model, so as to obtain position information of the single vertebra in the spine in the raw CT image, i.e., the first vertebra position information.

In step S130, an initial image of the single vertebra is acquired according to the first spine boundary information and the first vertebra position information.

For example, in step S130, the boundary information of the single vertebra is determined according to the first spine boundary information and the first vertebra position information, and an initial image of the single vertebra is obtained from a first spine image corresponding to the morphologically expanded spine image according to the boundary information of the single vertebra.

In a specific embodiment of the present application, the specific steps of acquiring the initial image of the single vertebra according to the first spine boundary information and the first vertebra position information are as follows:

Boundary information of each single vertebra is determined according to the first spine boundary information and the first vertebra position information.

The initial image of the single vertebra is acquired from the first spine image according to the boundary information of the single vertebra.

In step S140, the position of the single vertebra in the initial image of the single vertebra is marked, to generate an updated image of the single vertebra.

For example, in step S140, first, second spine boundary information is obtained, and then the position information of the single vertebra is updated according to the second spine boundary information. The position of the single vertebra in the initial image of the single vertebra is marked according to the updated position information of the single vertebra, to generate an updated image of the single vertebra.

In a specific embodiment of the present application, the specific steps of marking the position of the single vertebra in the initial image of the single vertebra to generate an updated image of the single vertebra are as follows:

The spine boundary information of the single vertebra in the initial image, i.e., second spine boundary information, is determined.

The position information of each single vertebra in the initial image of the single vertebra is updated according to the second spine boundary information.

The position of the single vertebra in the initial image of the single vertebra is marked according to the updated position information of the single vertebra, and a corresponding position marker image of the single vertebra in the body coordinate system is acquired. According to some embodiments, the position marker of each single vertebra in the initial image of the single vertebra is set with a corresponding pixel tag value.

An updated image of the single vertebra is generated according to the initial image of the single vertebra and the position marker image of the single vertebra.

In a specific embodiment of the present application, the specific steps of generating an updated image of the single vertebra according to the initial image of the single vertebra and the position marker image of the single vertebra are as follows:

The initial image of the single vertebra is transformed into an initial image of the single vertebra in the body coordinate system.

A third network model is constructed, and the initial image of the single vertebra in the body coordinate system and the position marker image of the single vertebra are superimposed, and are input into the third network model in a preset order, so that an updated image of the single vertebra is obtained by means of the third network model in the preset order.

The updated image of the single vertebra in the body coordinate system obtained by means of the third network model is transformed into an updated image of the single vertebra in the image coordinate system.

According to some embodiments, the updated image of the single vertebra includes a position marker of each single vertebra, and the position marker of each single vertebra contains a corresponding pixel tag value.

In step S150, the single vertebra in a restored image corresponding to the raw CT image is determined according to the updated image of the single vertebra.

For example, in step S150, the single vertebra in the raw image is marked in a preset order according to the single vertebra corresponding to the updated image of the single vertebra in the image coordinate system, and the single vertebra boundary information in the raw image is updated, to determine the single vertebra in a restored image corresponding to the raw image.

In a specific embodiment of the present application, the specific steps of determining the single vertebra in a restored image corresponding to the raw CT image according to the updated image of the single vertebra are as follows:

First, the acquired raw CT image is transformed into a raw image in the image coordinate system.

The single vertebra in the raw image is marked in a preset order according to the updated image of the single vertebra in the image coordinate system. According to some embodiments, a zero-pixel image of the same size as the raw image is generated according to the raw image in the image coordinate system. According to the preset order of outputting the updated images of the single vertebra by the third network model, the pixel value of the position marker of each single vertebra in the updated image of the single vertebra in the image coordinate system is replaced by the pixel tag value at a corresponding position in the zero-pixel image corresponding to the raw image, so that the position marker of each single vertebra in the updated image of the single vertebra is taken as the position marker of each single vertebra in the zero-pixel image corresponding to the raw image. Moreover, the pixel tag value corresponding to the position marker of each single vertebra in the zero-pixel image corresponding to the raw image is modified to the same value as the preset order of outputting the updated image of the single vertebra by the third network model. For example, the pixel tag value '1' of the position marker of each single vertebra in the zero-pixel image corresponding to the raw image is modified to 1, 2, 3 . . . .

After the position of each single vertebra in the zero-pixel image corresponding to the raw image is marked, a position marker of each single vertebra in the raw image is obtained accordingly.

The single vertebra boundary information in the raw image of the marked single vertebra is updated according to the updated image of the single vertebra in the image coordinate system, and the single vertebra boundary information in the raw image of the marked single vertebra is replaced with the single vertebra boundary information in the updated image of the single vertebra in the image coordinate system, so as to determine the single vertebra in the raw image. According to some embodiments, after the position marker of each single vertebra in the zero-pixel image corresponding to the raw image is obtained, a position marker of each single vertebra in the raw image can be obtained accordingly because the raw image in the image coordinate system is of the same size as the corresponding zero-pixel image. Corresponding boundary information of each single vertebra is obtained from the updated image of the single vertebra in the image coordinate system, and the boundary information of each single vertebra in the raw image is replaced with the boundary information of each single vertebra in the updated image of the single vertebra in the image coordinate system. Then, the single vertebra in the raw image can be determined according to the position marker of each single vertebra in the raw image and the boundary information of each single vertebra in the raw image after the replacement.

Figure 2:
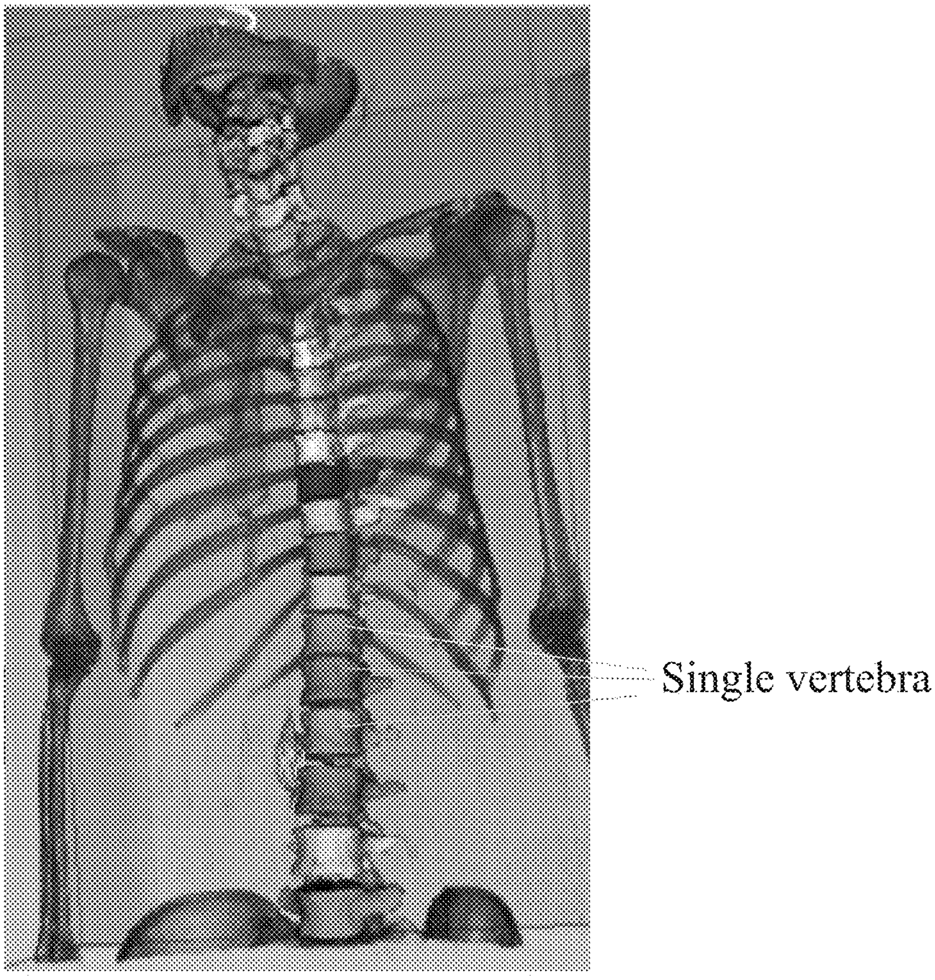
FIG. 2 shows a display effect of a single vertebra according to an example embodiment of the present application.

After each single vertebra in the raw image is determined, the raw image of the determined single vertebra is taken as the restored image corresponding to the raw CT image. According to some embodiments, each single vertebra in the restored image is determined and displayed in the restored image with a pixel tag value that is the same as the preset order of outputting the updated image of the single vertebra by the third network model. For the display of each single vertebra in the restored image, please see the display effect of a single vertebra as shown in FIG. 2.

According to the embodiments of the present application, the technical scheme of the present application can segment the spine in the CT image on a single segment basis by means of neural network models, so that each single vertebra in the spine can be acquired rapidly, and the segmentation accuracy is improved.

Figure 3:
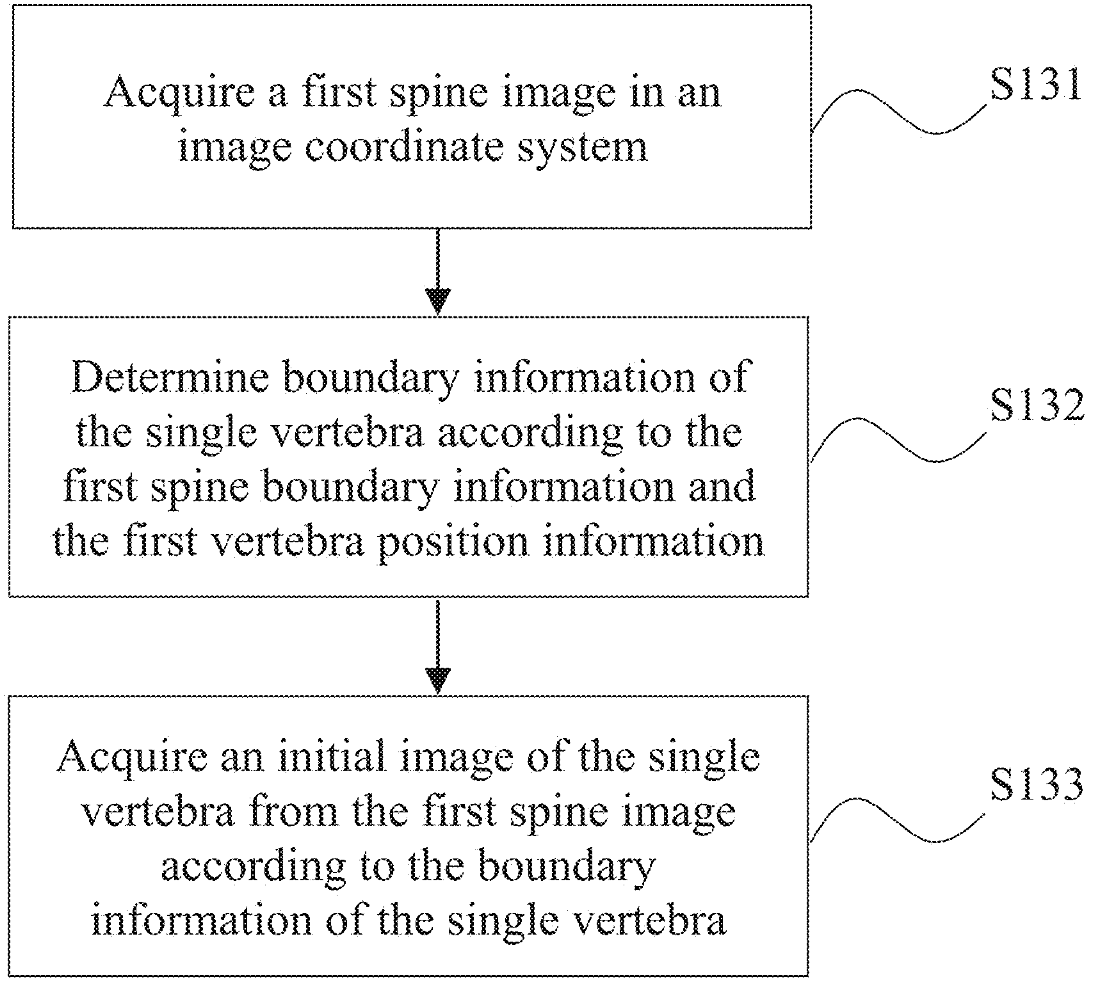
FIG. 3 shows a flowchart of acquiring an initial image of a single vertebra according to an example embodiment of the present application.

FIG. 3 shows a flowchart of acquiring an initial image of a single vertebra according to an example embodiment of the present application.

As shown in FIG. 3, in step S131, a first spine image in an image coordinate system is acquired.

For example, in step S131, a morphologically expanded spine image is obtained, and the morphologically expanded spine image in the body coordinate system is transformed into a first spine image in the image coordinate system.

In step S132, boundary information of the single vertebra is determined according to the first vertebra boundary information and the first vertebra position information.

For example, in step S132, boundary information of a morphologically expanded spine image (i.e., the first spine boundary information) and position information of the single vertebra in the spine (i.e., the first vertebra position information) are obtained, and boundary information of each single vertebra is determined accordingly.

In a specific embodiment of the present application, after the morphologically expanded spine image is obtained by means of the first network model, first spine boundary information corresponding to the morphologically expanded spine image is obtained, wherein the first spine boundary information includes upper boundary 'top' and lower boundary 'bottom' of the spine in the Z-axis direction.

After the first vertebra position information is obtained by means of the second network model, boundary information of the single vertebra in the X-axis, Y-axis and Z-axis directions is determined according to the first vertebra position information and the obtained first spine boundary information, wherein the boundaries of the single vertebra in the X-axis and Y-axis directions are consistent with the boundaries of the morphologically expanded spine image in the X-axis and Y-axis directions.

According to some embodiments, the first vertebra position information is obtained by means of the second network model, and then each single vertebra in the spine is sorted sequentially in the Z-axis direction, and the sorting result is denoted as 'order'.

According to some embodiments, upper boundary 'top' and lower boundary 'bottom' in the Z-axis direction in the first spine boundary information are acquired. If the single vertebra is in the first place in the sorting result, the corresponding coordinate range in the Z-axis direction is [bottom, order[i+1].z]; if the single vertebra is in the last place in the sorting result, the corresponding coordinate range in the Z-axis direction is [order[i−1].z, top]; if the single vertebra is in any place except the first place and the last place in the sorting result, the corresponding coordinate range in the Z-axis direction is [order[i−1], order[i+1].z], where, order[i].z represents the coordinate of the ith single vertebra corresponding to the sorting result in the Z-axis direction.

The coordinate range [curminz, curmaxz] of the single vertebra in the Z-axis direction i.e., the boundary information of the single vertebra in the Z-axis direction, is determined according to the sorting result.

In step S133, an initial image of the single vertebra is obtained from the first spine image according to the boundary information of the single vertebra.

For example, in step S133, an initial image of each single vertebra is extracted from the first spine image according to the boundary information of the single vertebra, wherein the boundaries of the initial image of the single vertebra in the X-axis direction and the Y-axis direction are consistent with the boundaries of the first spine image in the X-axis direction and the Y-axis direction.

Figure 4:
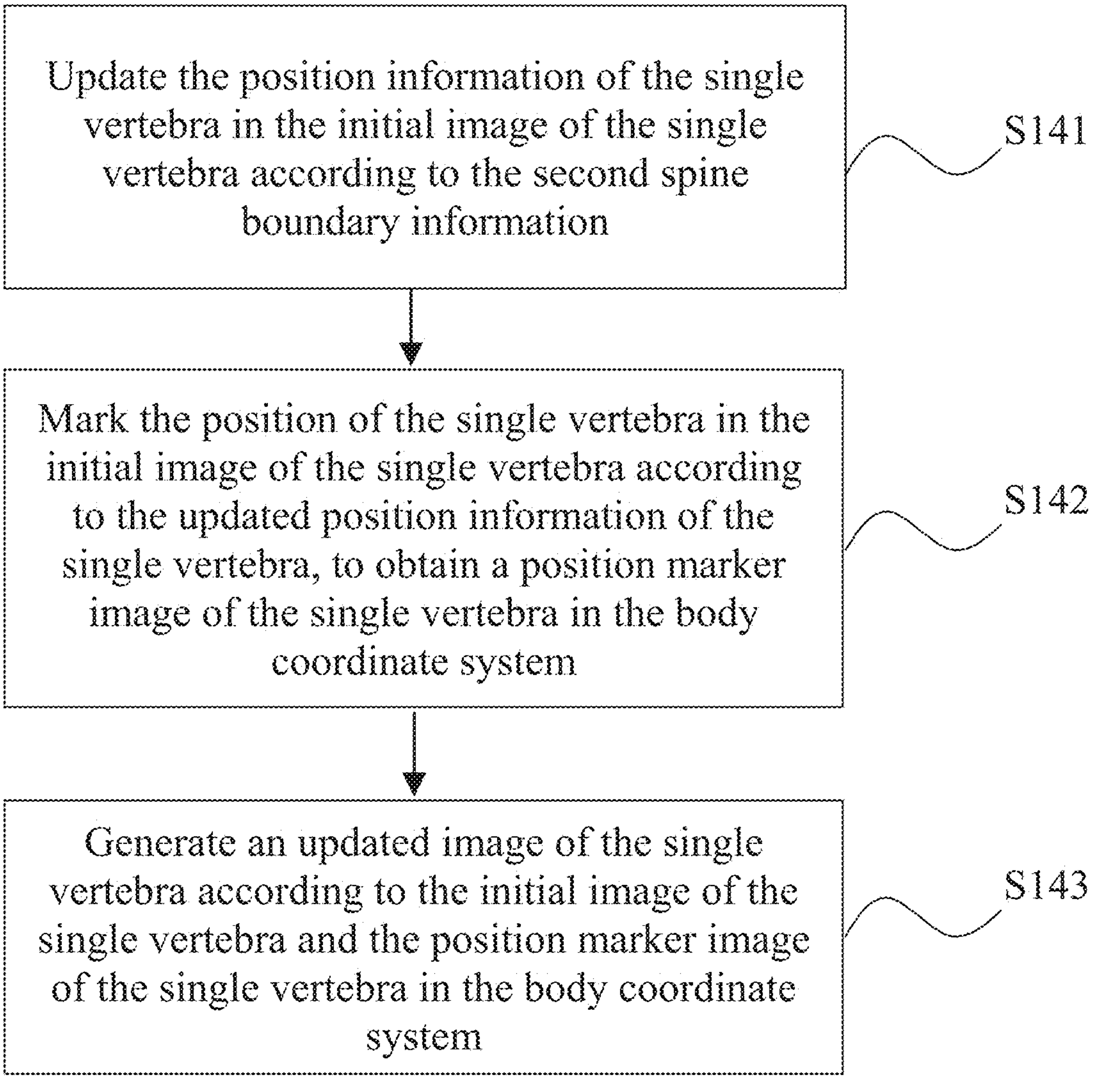
FIG. 4 shows a flowchart of acquiring an updated image of the single vertebra according to an example embodiment of the present application.

FIG. 4 shows a flowchart of acquiring an updated image of the single vertebra according to an example embodiment of the present application.

As shown in FIG. 4, in step S141, the position information of the single vertebra in the initial image of the single vertebra is updated according to the second spine boundary information.

For example, in step S141, the spine boundary information in the initial image of the single vertebra, i.e., second spine boundary information, is obtained, and the position information of each single vertebra in the initial image of the single vertebra is updated according to the second spine boundary information.

In a specific embodiment of the present application, the second spine boundary information is determined according to the initial image of the single vertebra.

According to some embodiments, the spine boundary information in the initial image of the single vertebra may be obtained with the numpy.where( ) method in a numpy scientific computing library.

The position information of each single vertebra in the initial image of single vertebra is updated according to the second spine boundary information.

In step S142, the position of the single vertebra in the initial image of the single vertebra is marked according to the updated position information of the single vertebra, to obtain a position marker image of the single vertebra in the body coordinate system.

For example, in step S142, the position of the single vertebra in the initial image of the single vertebra is marked according to the updated position information of the single vertebra, and the position marker of the single vertebra is obtained. The initial image of the single vertebra containing the position marker of the single vertebra is transformed into a position marker image of the single vertebra in the body coordinate system.

In a specific embodiment of the present application, the position marker of the single vertebra in the initial image of the single vertebra is obtained according to the updated position information of the single vertebra.

According to some embodiments, first, a zero-pixel image of the same size as the initial image of the single vertebra in the image coordinate system is generated. Each single vertebra is marked in the zero-pixel image according to the updated position information of the single vertebra, to obtain a position marker image of the single vertebra in the image coordinate system.

According to some embodiments, for each single vertebra in the zero-pixel image, a point corresponding to the updated position coordinates of the single vertebra may be taken as a center of sphere, and a sphere having a radius within a preset numerical range (may be adjusted according to the actual need, for example, the preset numerical range may be [1,7]) may be set to replace the point corresponding to the position coordinates of the single vertebra in the zero-pixel image and used as a position marker of the single vertebra, and the pixel tag value of the sphere is set to 1. The initial image of the single vertebra is superimposed with the zero-pixel image in which the position of the single vertebra is marked to obtain a position marker of the single vertebra in the initial image of the single vertebra.

The initial image of the single vertebra containing the position marker of the single vertebra is transformed into a position marker image of the single vertebra in the body coordinate system.

In step S143, an updated image of the single vertebra is generated according to the initial image of the single vertebra and the position marker image of the single vertebra in the body coordinate system.

For example, in step S143, the initial image of the single vertebra is transformed into an initial image of the single vertebra in the body coordinate system. The initial image of the single vertebra in the body coordinate system and the position marker image of the single vertebra in the body coordinate system are superimposed and inputted into a third network model, and an updated image of the single vertebra is obtained by means of the third network model.

In a specific embodiment of the present application, a third network model is constructed, and the obtained initial image of the single vertebra is transformed into an initial image of the single vertebra in the body coordinate system.

The initial image of the single vertebra in the body coordinate system and the position marker image of the single vertebra in the body coordinate system are superimposed and inputted into the third network model in a preset order, and an updated image of the single vertebra is acquired by means of the third network model in the preset order of data input.

According to some embodiments, the updated image of the single vertebra includes a position marker of each single vertebra, and the position marker of each single vertebra contains a corresponding pixel tag value.

Figure 5:
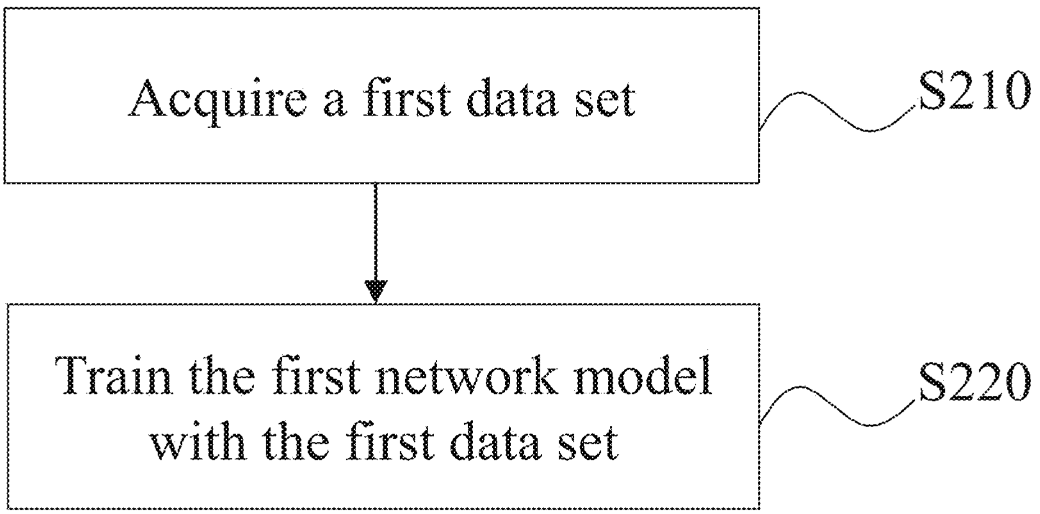
FIG. 5 shows a flowchart of training a first network model according to an example embodiment of the present application.

FIG. 5 shows a flowchart of training a first network model according to an example embodiment of the present application.

As shown in FIG. 5, in step S210, a first data set is acquired.

For example, in step S210, a first data set is acquired from a public data set according to a preset specification for training a first network model.

In a specific embodiment of the present application, a first data set is acquired from a public data set, wherein the first data set includes a variety of types of spine CT images and standard position information of each single vertebra in the spine CT images, wherein the standard position information of each single vertebra is the position information in the image coordinate system.

According to some embodiments, the preset specification for obtaining spine CT images may be 512*512*N, where N represents the number of layers of the CT image data, and 512*512 represents the size of each layer of the CT image data.

According to some embodiments, the variety of types of spine CT images included in the first data set correspond to CT images of a spine including all ribs from cervical vertebrae to sacral vertebrae; CT images of a spine including all ribs, some thoracic vertebrae and some lumbar vertebrae, but excluding sacral vertebrae; and CT images of a spine including all sacral vertebrae, some thoracic vertebrae and some lumbar vertebrae, but excluding ribs.

According to some embodiments, in order to avoid a categorization error of the spine and the sacra caused by lumbarization of the sacral vertebrae, the first data set further includes CT images of a spine including all ribs from cervical vertebrae to sacral vertebrae and involving sacral vertebrae that have transformed into lumbar vertebrae.

In step S220, a first network model is trained with the first data set.

For example, in step S220, a first network model is set, and the first network model is trained with the obtained first data set.

Figure 6:
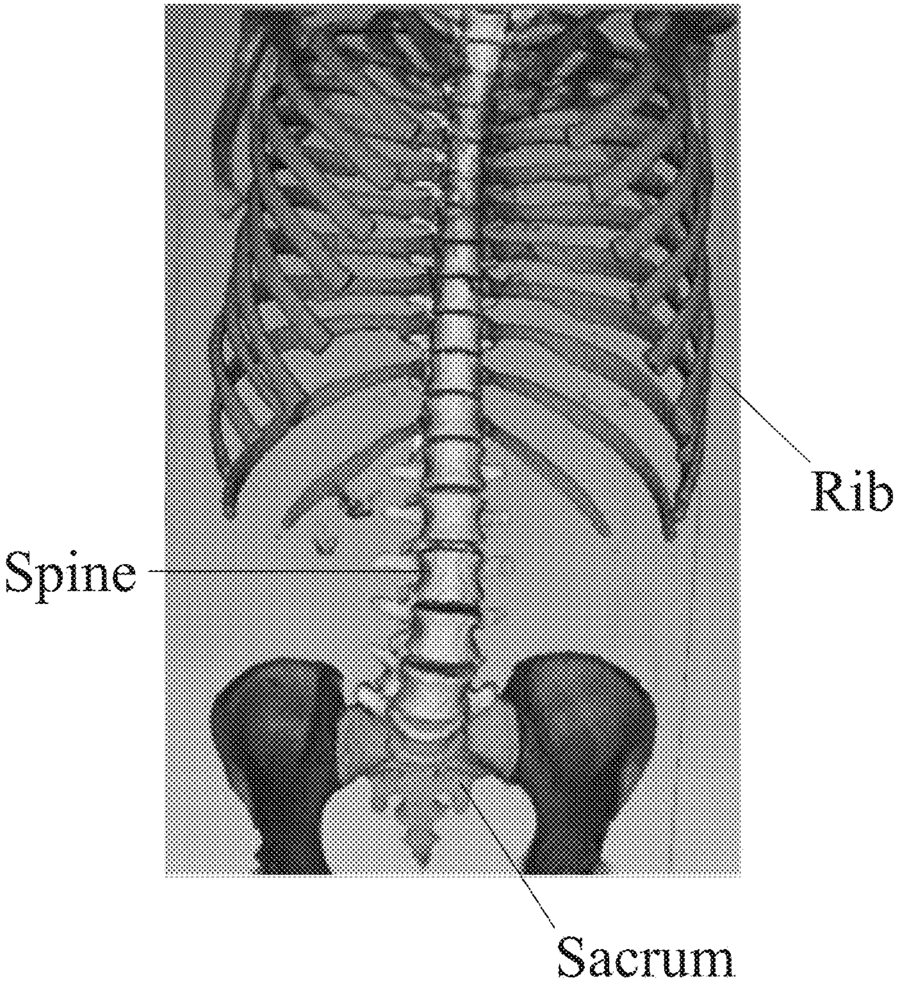
FIG. 6 shows a segmentation effect of spine, sacra and ribs according to an example embodiment of the present application.

In a specific embodiment of the present application, after the first network model is constructed, the spine CT images in the first data set are inputted into the first network model, and a segmentation result of spine, sacra and ribs in the spine CT images is obtained by means of the first network model. For the segmentation result of spine, sacra and ribs in spine CT images, please see the segmentation effect of spine, sacra and ribs as shown in FIG. 6.

According to some embodiments, the first network model may employ an nnUNet neural network model.

Figure 7:
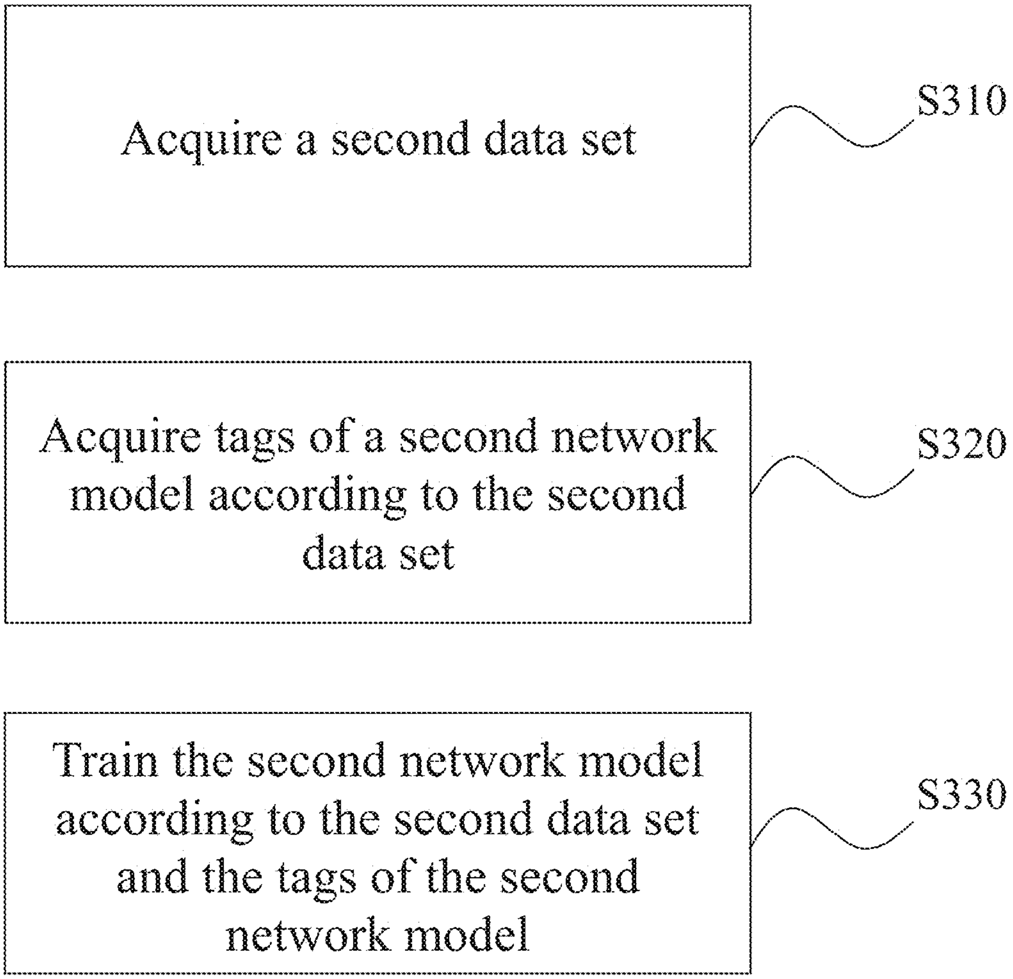
FIG. 7 shows a flowchart of training a second network model according to an example embodiment of the present application.

FIG. 7 shows a flowchart of training a second network model according to an example embodiment of the present application.

As shown in FIG. 7, in step S310, a second data set is acquired.

For example, in step S310, a second data set is acquired from a public data set according to a preset specification for training a second network model.

In a specific embodiment of the present application, a second data set is acquired from a public data set, wherein the second data set includes a variety of types of spine CT images and standard position information of each single vertebra in the spine CT images, wherein the standard position information of each single vertebra is the position information in the image coordinate system.

According to some embodiments, the preset specification for obtaining spine CT images may be 512*512*N, where N represents the number of layers of the CT image data, and 512*512 represents the size of each layer of the CT image data.

According to some embodiments, the variety of types of spine CT images included in the second data set correspond to CT images of a complete spine from cervical vertebrae to sacral vertebrae; CT images of a spine including some cervical vertebrae and some thoracic vertebrae; CT images of a spine including some thoracic vertebrae and some lumbar vertebrae; and CT images of a spine including some thoracic vertebrae and all lumbar vertebrae.

In step S320, tags of the second network model are obtained according to the second data set.

For example, in step S320, the spine CT images in the second data set are transformed into spine images in the image coordinate system. Each single vertebra in the spine images in the image coordinate system is marked according to standard position information of each single vertebra. Tags of the second network model are generated according to the spine images in which each single vertebra is marked.

In a specific embodiment of the present application, the spine CT images in the second data set in the body coordinate system are transformed into spine images in the image coordinate system.

According to some embodiments, the transformation between the body coordinate system and the image coordinate system may be realized by invoking the application program interface (API) of corresponding software, such as a python runtime library SimpleITK.

Furthermore, a zero-pixel image of the same size as the spine image in the image coordinate system is generated.

The position of each single vertebra in the spine is marked in the zero-pixel image according to the standard position information of each single vertebra.

According to some embodiments, for each single vertebra in the zero-pixel image, a point corresponding to the standard position coordinates of the single vertebra may be taken as a center of sphere, and a sphere having a radius within a preset numerical range (may be adjusted according to the actual need, for example, the preset numerical range may be [1,7]) may be rendered to replace the point corresponding to the position coordinates of the single vertebra in the zero-pixel image and used as a position marker of the single vertebra, and the pixel tag value of the sphere is set to 1.

The spine image in the image coordinate system is superimposed with the zero-pixel image in which the position of each single vertebra in the spine is marked, and a position marker image of each single vertebra in the spine in the image coordinate system is obtained.

The position marker image of each single vertebra in the image coordinate system is transformed into a position marker image of each single vertebra in the body coordinate system, which is used as a tag of the second network model.

In step S330, a second network model is trained according to the second data set and the tags of the second network model.

For example, in step S330, a second network model is set, and the second network model is trained with the second data set and the tags of the second network model.

Figure 8:
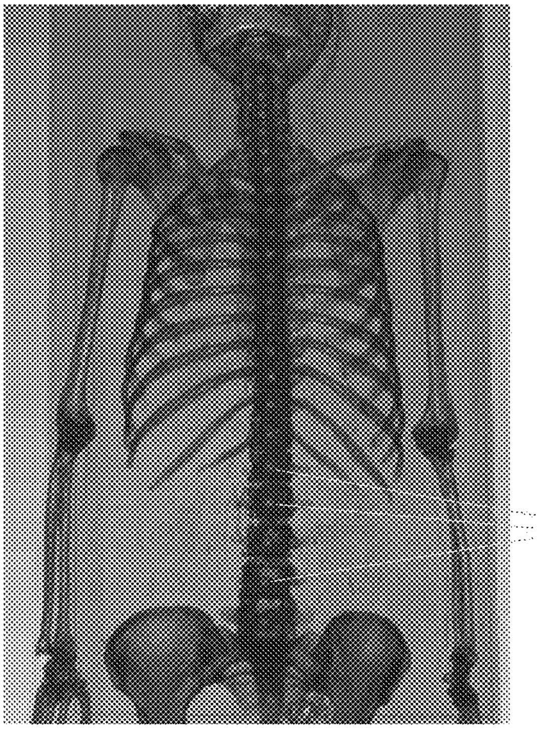
FIG. 8 shows a rendering effect of position information of the single vertebra in the spine according to an example embodiment of the present application.

In a specific embodiment of the present application, after the second network model is set, the CT images of spines in the second data set are inputted into the second network model, and position information of each single vertebra in the spine CT images is outputted by means of the second network model by using the position marker image of each single vertebra in the body coordinate system as a tag. For the position of each single vertebra in the spine CT images, please see the rendering effect of the position information of a single vertebra in the spine as shown in FIG. 8.

Figure 9:
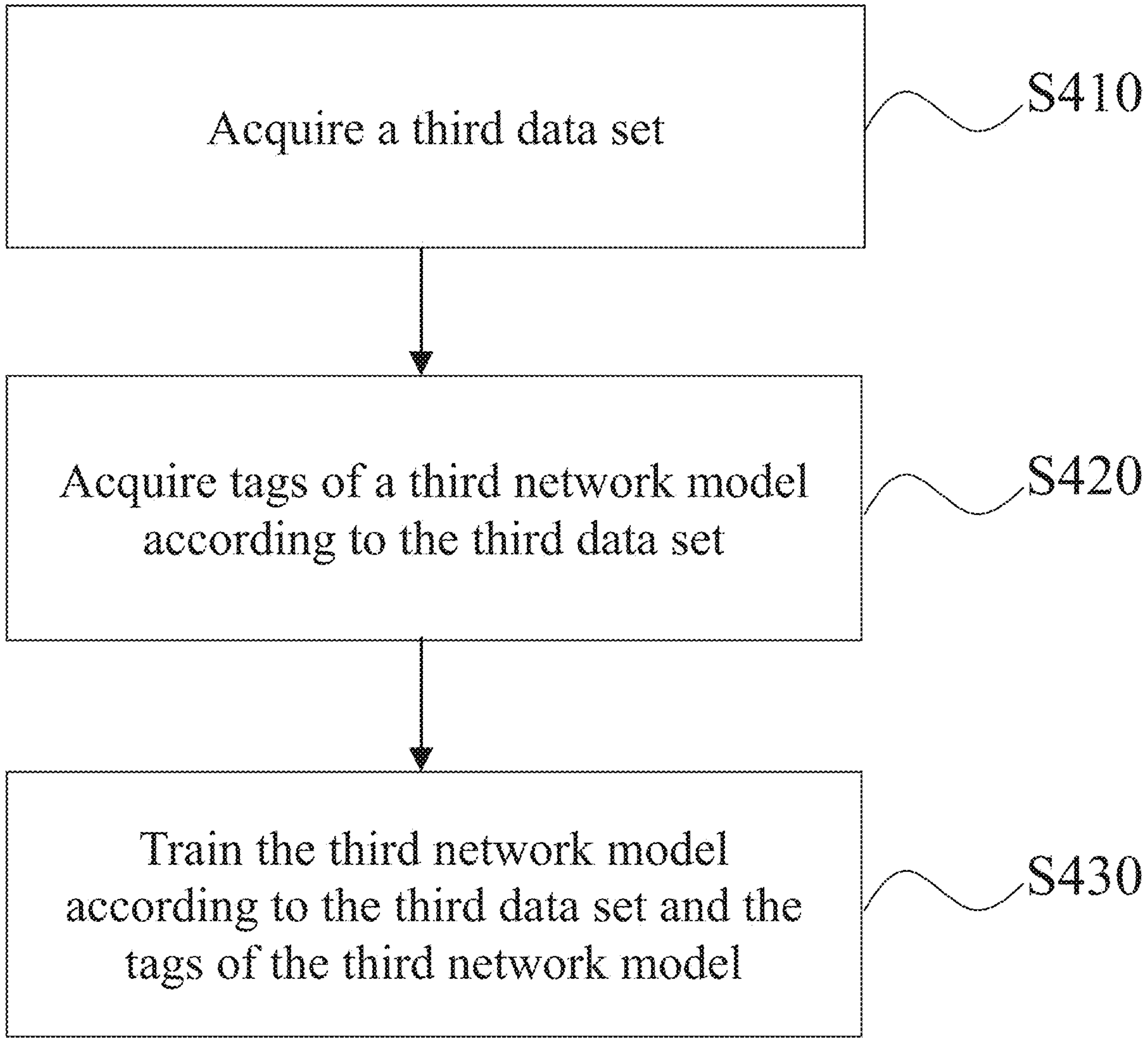
FIG. 9 shows a flowchart of training a third network model according to an example embodiment of the present application.

FIG. 9 shows a flowchart of training a third network model according to an example embodiment of the present application.

As shown in FIG. 9, in step S410, a third data set is acquired.

For example, in step S410, a third data set is acquired from a public data set according to a preset specification for training a third network model.

In a specific embodiment of the present application, a third data set is acquired from a public data set, wherein the third data set includes multi-category spine CT images, standard position information of each single vertebra in the spine CT images and segmentation tag information of each segment of spine in the spine CT images, wherein the standard position information of each single vertebra and segmentation tag information of each segment of spine in the spine CT images are position information in the image coordinate system.

According to some embodiments, the variety of types of spine CT images included in the third data set correspond to CT images of a spine including all segments of complete cervical vertebrae; CT images of a spine including all segments of complete thoracic vertebrae; and CT images of a spine including all segments of complete cervical vertebrae.

In step S420, tags of the third network model are acquired according to the third data set.

For example, in step S420, the spine CT images in the third data set are transformed into spine images in the image coordinate system. The spine images in image coordinate system are segmented according to the segmentation tag information of each segment of the spine to obtain the image of each single segment of the spine. The pixels of the image of each single vertebra are processed, and the pixel-processed image of the single vertebra is used as a tag of the third network model.

In a specific embodiment of the present application, after the spine CT images in the third data set are transformed into spine images in the image coordinate system, position information of each single vertebra in the spine images in the image coordinate system is obtained according to the segmentation tag information of each segment of the spine.

According to some embodiments, the position information of each single vertebra in the spine images in the image coordinate system may be implemented with the numpy.where( ) method in a numpy scientific computing library. The position coordinates Position of a single vertebra may be obtained as follows:

position=[[min_z, max_z],[min_y, max_y],[min_x, max_*x*]]

Where, 'min' represents minimum position coordinates of the single vertebra, and 'max' represents maximum position coordinates of the single vertebra.

The image of each single vertebra in the image coordinate system is obtained according to the position information of each single vertebra.

The pixel values of the regions except the vertebra region in the image of each single vertebra in the image coordinate system are set to zero, and the image with the pixel values set to zero is superimposed with the image of each single vertebra in the image coordinate system to generate a tag image of the single vertebra in the image coordinate system.

The tag image of the single vertebra in the image coordinate system is transformed into a tag image of the single vertebra in the body coordinate system, which is used as a tag of the third network model.

In step S430, a third network model is trained according to the third data set and the tags of the third network model.

For example, in step S430, a third network model is set, and the third network model is trained with the third data set and the tags of the third network model.

In a specific embodiment of the present application, the image of each single vertebra in the image coordinate system obtained in step S420 is transformed into an image of each single vertebra in the body coordinate system and used as an input data for the third network model.

According to some embodiments, the voxel spacing and direction in the image of the single vertebra in the body coordinate system are consistent with the voxel spacing and direction in the spine CT images in the third data set.

First, the image size of the single vertebra in the body coordinate system is calculated. The image size of the single vertebra in each dimension in the image coordinate system is multiplied by the voxel spacing in the spine CT images in the third data set to obtain an image size of the single vertebra in the body coordinate system, and the calculation result is denoted as 'newsize'.

According to the image size of the single vertebra in the body coordinate system, the position of a center point of the image of the single vertebra in the body coordinate system is calculated with the following formula, and the center point of the image of the single vertebra in the body coordinate system is denoted as 'origin', $$\text{origin}[i] = \text{direction}[i][0] * new_{size[0]} + \text{direction}[i][1] * new_{size[1]} + \text{direction}[i][2] * new_{size[2]}$$

Where i=1, 2, 3, and 'direction' is the direction of the spine CT image in the third data set.

Figure 10:
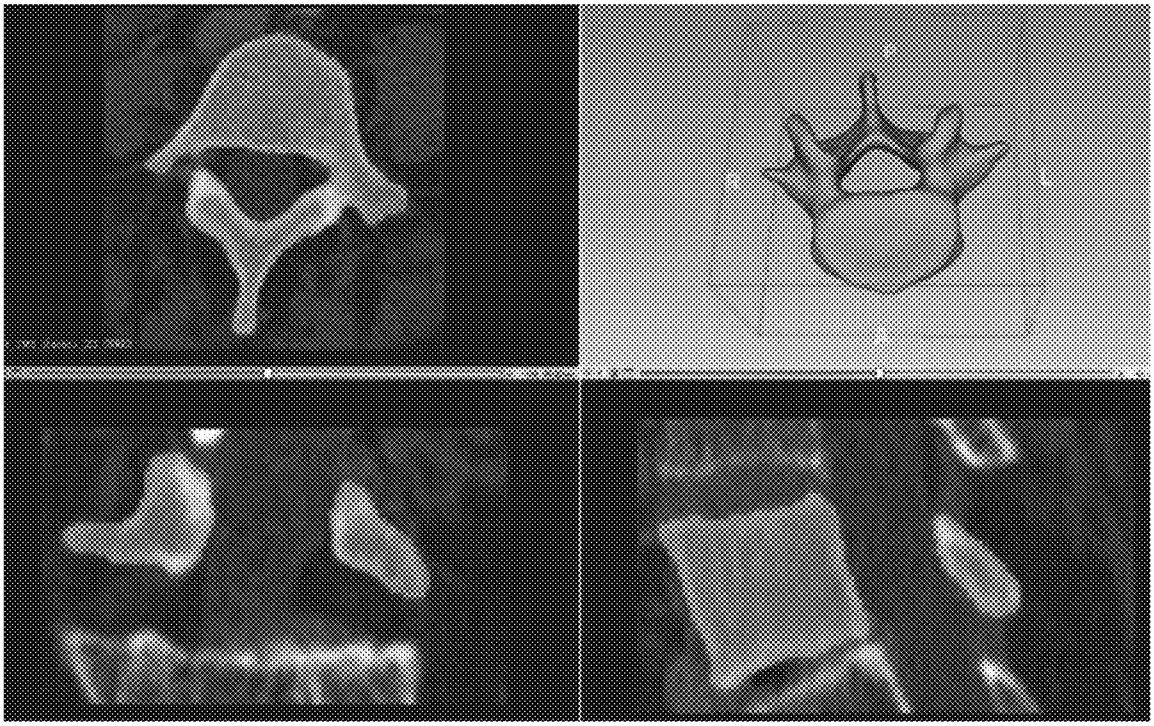
FIG. 10 shows a schematic diagram of the single vertebra according to an example embodiment of the present application.

The image of each single vertebra in the image coordinate system is transformed into an image of each single vertebra in the body coordinate system according to the obtained voxel spacing and direction, and the position of the center point of the image obtained through calculation. For the image of each single vertebra in the body coordinate system, please see the schematic diagram of a single vertebra in the body coordinate system as shown in FIG. 10.

Based on the standard position information of each single vertebra, the position information of each single vertebra in the image coordinate system is updated.

According to some embodiments, the standard position information of a single vertebra in the third data set is denoted as spine_pos(x, y, z), and the position information of a single vertebra in the updated image of the single vertebra is denoted as spine_pos(x1, y1, z1), and the position information of a single vertebra in the updated image of the single vertebra is calculated with the following formula.

$$\begin{cases} x_1 = x - \text{min\_x} \\ y_1 = y - \text{min\_y} \\ z_1 = z - \text{min\_z} \end{cases}$$

Where, 'min' represents minimum position coordinates of the single vertebra, and 'max' represents maximum position coordinates of the single vertebra.

A zero-pixel image of the same size as the image of each single vertebra in the image coordinate system is generated.

The position of each single vertebra is marked in the zero-pixel image according to the updated position information of the single vertebra, to obtain a position marker image of the single vertebra in the image coordinate system.

According to some embodiments, for each single vertebra in the zero-pixel image, a point corresponding to the updated position coordinates of the single vertebra may be taken as a center of sphere, and a sphere having a radius within a preset numerical range (may be adjusted according to the actual need, for example, the preset numerical range may be

[1,7]) may be rendered to replace the point corresponding to the position coordinates of the single vertebra in the zero-pixel image and used as a position marker of the single vertebra, and the pixel tag value of the sphere is set to 1. The image of each single vertebra in the image coordinate system is superimposed with the zero-pixel image in which the position of the single vertebra is marked, and a position marker image of the single vertebra in the image coordinate system is obtained.

The position marker image of the single vertebra in the image coordinate system is transformed into a position marker image of the single vertebra in the body coordinate system, which is used as another input data for the third network model.

The image of each single vertebra in the body coordinate system and the position marker image of the single vertebra in the body coordinate system are superimposed and inputted into the third network model, and the third network model is trained according to the tags of the third network model.

Figure 11:
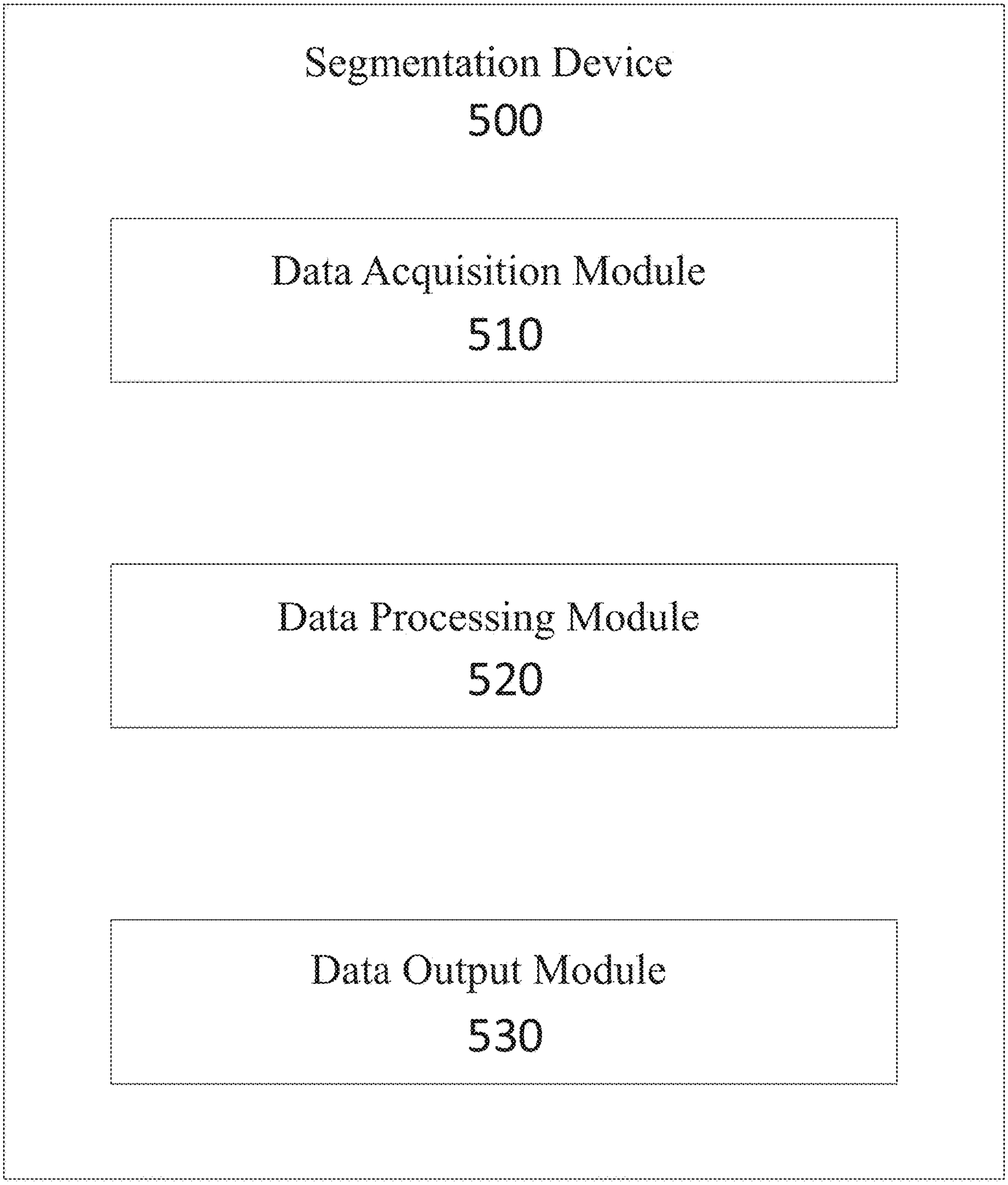
FIG. 11 shows a block diagram of a single vertebra segmentation device according to an example embodiment of the present application.

FIG. 11 shows a block diagram of a single vertebra segmentation device according to an example embodiment of the present application.

As shown in FIG. 11, a segmentation device 500 comprises a data acquisition module 510, a data processing module 520 and a data output module 530.

The data acquisition module 510 is configured for acquiring a raw CT image.

According to some embodiments, the data acquisition module 510 is further configured for acquiring a first data set from a public data set for training a first network model, acquiring a second data set from a public data set for training a second network model, and acquiring a third data set from a public data set for training a third network model.

The data processing module 520 constructs a first network model and trains the first network model.

The data processing module 520 obtains a segmentation result of spine, sacra and ribs in the raw CT image by means of the first network model, and performs morphological expansion on the spine in a segmented image obtained through segmentation of the raw CT image according to the segmentation result to obtain a morphologically expanded spine image and first spine boundary information corresponding to the morphologically expanded spine image.

The data processing module 520 constructs a second network model and trains the second network model.

The data processing module 520 obtains position information of the single vertebra in the raw CT image, i.e., first vertebra position information, by means of the second network model.

The data processing module 520 determines boundary information of the single vertebra according to the first spine boundary information and the first vertebra position information, and obtains an initial image of the single vertebra from the first spine image in the image coordinate system transformed from the morphologically expanded spine image according to the boundary information of the single vertebra.

After second spine boundary information corresponding to the initial image of the single vertebra is determined, the data processing module 520 updates the position information of the single vertebra in the initial image of the single vertebra, and obtains a position marker of the single vertebra in the initial image of the single vertebra.

The data processing module 520 transforms the initial image of the single vertebra containing the position marker of the single vertebra into a position marker image of the single vertebra in a body coordinate system, and transforms the initial image of the single vertebra into an initial image of the single vertebra in the body coordinate system.

The data processing module 520 constructs a third network model and trains the third network model.

The data processing module 520 superimposes the initial image of the single vertebra in the body coordinate system and the position marker image of the single vertebra in the body coordinate system and input a result of the superimposition into the third network model in a preset order, and obtains an updated image of the single vertebra by means of the third network model. Moreover, the data processing module 520 transforms the updated image of the single vertebra in the body coordinate system obtained by means of the third network model into an updated image of the single vertebra in an image coordinate system.

The data processing module 520 transforms the raw CT image into a raw image in the image coordinate system, and determines each single vertebra in the raw image according to the updated image of the single vertebra in the image coordinate system and marks the single vertebra in a preset order.

The data output module 530 outputs the determined raw image of each single vertebra as a restored image corresponding to the raw CT image.

Figure 12:
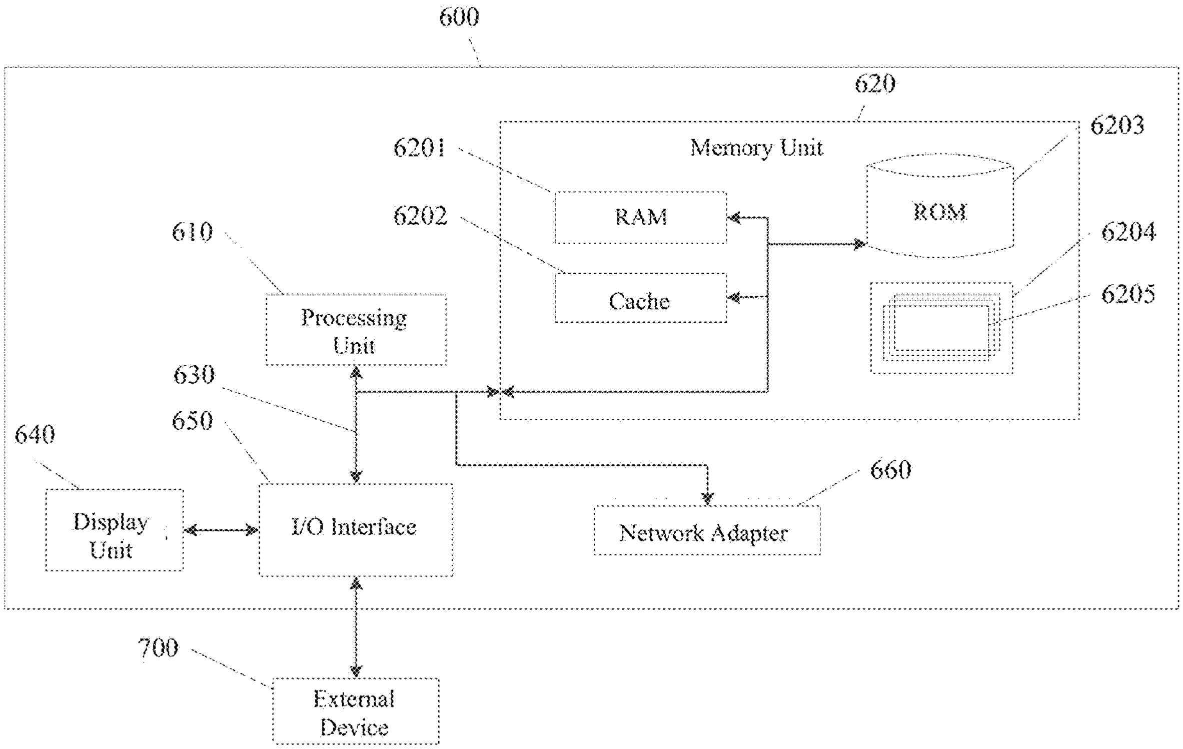
FIG. 12 shows a block diagram of an electronic device according to an example embodiment of the present application.

FIG. 12 shows a block diagram of an electronic device according to an example embodiment of the present application.

As shown in FIG. 12, the electronic device 600 is just an example, and should not be understood as imposing as any limitation on the function and application scope of the embodiments of the present application.

As shown in FIG. 12, the electronic device 600 is embodied in the form of a general-purpose computing device. Components of the electronic device 600 may include, but are not limited to: at least one processing unit 610, at least one memory unit 620, a bus 630 connecting different system components (including the memory unit 620 and the processing unit 610), a display unit 640, and the like. The memory unit stores program codes, which can be executed by the processing unit 610, so that the processing unit 610 is instructed to perform the methods described in various example embodiments of the present application. For example, the processing unit 610 may perform the method as shown in FIG. 1.

The memory unit 620 may include a readable medium in the form of a volatile memory unit, such as a random-access memory (RAM) unit 6201 and/or a cache unit 6202, and may further include a read-only memory (ROM) unit 6203.

The memory unit 620 may also include a program/utility 6204 having a set of (at least one) program modules 6205, and such program modules 6205 may include, but are not limited to: an operating system, one or more application programs, other program modules, and program data, each or a combination of which may include the implementation of a network environment.

The bus 630 may represent one or more of several types of bus structures, including a memory unit bus or a memory unit controller, a peripheral bus, a graphics acceleration port, a processing unit, or a local bus using any of a variety of bus structures.

The electronic device 600 may further communicate with one or more external devices 700 (e.g., a keyboard, a pointing device, a Bluetooth device, etc.), and may further communicate with one or more devices that enable users to interact with the electronic device 600, and/or communicate with any device that enables the electronic device 600 to communicate with one or more other computing devices (e.g., a router, a modem, etc.). Such communication may be carried out through an input/output (I/O) interface 650. Moreover, the electronic device 600 may further communicate with one or more networks (e.g., a local area network (LAN), a wide area network (WAN) and/or a public network, such as the Internet) through a network adapter 660. The network adapter 660 may communicate with other modules of the electronic device 600 through the bus 630. It should be understood that although not shown in the figure, other hardware and/or software modules may be used in conjunction with the electronic device 600, including, but not limited to: micro-codes, device drivers, redundant processing units, external disk drive arrays, a RAID system, a tape drive and a data backup storage system.

Through the description of the above embodiments, it is easy for those skilled in the art to understand that the example embodiments described herein may be implemented in the form of software or in the form of software combined with necessary hardware. The technical scheme according to the embodiments of the present application may be embodied in the form of a software product, which can be stored in a nonvolatile storage medium (e.g., a CD-ROM, a U disk, a mobile hard disk, etc.) or in a network, and includes several instructions to instruct a computing device (e.g., a personal computer, a server, a mobile terminal or a network device, etc.) to execute the method according to the embodiments of the present application.

The software product may employ any readable medium or any combination of readable media. The readable medium may be a readable signal medium or a readable storage medium. The readable storage medium may be, for example, but not limited to, an electrical, magnetic, optical, electromagnetic, infrared, or semiconductor system, device or component, or any combination thereof. More specific examples (a non-exhaustive list) of the readable storage media include: an electrical connection with one or more conductive wires, a portable disk, a hard disk, a random-access memory (RAM), a read-only memory (ROM), an erasable programmable read-only memory (EPROM or flash memory), an optical fiber, a portable compact disk read-only memory (CD-ROM), an optical storage device, a magnetic storage device, or any suitable combination thereof.

The computer-readable storage medium may include data signals propagating in a baseband or as part of a carrier wave, in which readable program codes are carried. The propagated data signals may take a variety of forms, including, but not limited to, electromagnetic signals, optical signals or any suitable combination thereof. Alternatively, the readable storage medium may be any readable medium that can emit, propagate or transmit a program for use by or in combination with an instruction execution system, device or component, other than a readable storage medium. The program codes contained in the readable storage medium may be transmitted through any suitable medium, including but not limited to a wireless connection, a wired connection, an optical cable, RF, etc., or any suitable combination thereof.

The program codes for performing the operations in the present application may be written in any programming language or any combination of programming languages, including object-oriented programming languages, such as Java, C++, and conventional procedural programming languages, such as C language or similar programming languages. The program codes may be executed completely on a user computing device, partially executed on a user device, executed as an independent software package, partially executed on a user computing device and partially executed on a remote computing device, or completely executed on a remote computing device or a server. In the case that a remote computing device is involved, the remote computing device may be connected to a user computing device through any kind of network, including a local area network (LAN) or a wide area network (WAN), or may be connected to an external computing device (e.g., through the Internet provided by an Internet service provider).

The computer-readable medium carries one or more programs, which, when executed by the device, instructs the computer-readable medium to implement the aforementioned functions.

Those skilled in the art can understand that the above modules may be distributed in devices according to the description of the embodiment, or may reside in one or more devices that are different from the devices in the embodiment. The modules in the above embodiment may be integrated into one module or further divided into a plurality of sub-modules.

According to some embodiments of the present application, the technical scheme of the present application may perform single-segment segmentation on the spine by means of a convolution network model on a premise of ensuring speed and accuracy, so as to obtain the image of a corresponding single vertebra and improve the accuracy of spine segmentation.

While some embodiments of the present application are described above in detail, the description of the above embodiments is only intended to assist in understanding the method and its core idea in the present application. Besides, those skilled in the art can make various modifications or variations according to the idea of the present application and based on the specific embodiments and application scope of the present application; however, all such modifications or variations shall be deemed as falling in the scope of protection of the present application. In conclusion, the content of this specification should not be construed as limiting the present application.

What is claimed is:

1. A single vertebra segmentation method, comprising:

acquiring first spine boundary information, which is boundary information of a spine in a segmentation result obtained through image segmentation of a raw CT image;

acquiring first vertebra position information, which is information on the position of a single vertebra in the spine in the raw CT image;

acquiring an initial image of the single vertebra according to the first spine boundary information and the first vertebra position information;

marking the position of the single vertebra in the initial image of the single vertebra to generate an updated image of the single vertebra; and determining the single vertebra in a restored image corresponding to the raw CT image according to the updated image of the single vertebra;

wherein the raw CT image is a reconstructed 3D image volume processed from raw sinogram data generated by computed tomography;

wherein determining the single vertebra in a restored image corresponding to the raw CT image according to the updated image of the single vertebra comprises:

transforming the raw CT image into a raw image in an image coordinate system;

acquiring a zero-pixel image corresponding to the raw image;

marking the single vertebra in the zero-pixel image according to the updated image of the single vertebra in the image coordinate system;

acquiring a position marker of the single vertebra in the raw image according to the zero-pixel image corresponding to the raw image of the marked single vertebra;

updating single vertebra boundary information in the raw image of the marked single vertebra according to the updated image of the single vertebra in the image coordinate system to determine the single vertebra in the raw image; and taking the raw image of the determined single vertebra as the restored image;

wherein the raw image is obtained by transforming the raw CT image in the image coordinate system.

2. The single vertebra segmentation method according to claim 1, wherein acquiring first spine boundary information comprises:

constructing a first network model;

acquiring a segmentation result of spine, sacra and ribs in the raw CT image by means of the first network model to obtain a segmented image of the raw CT image;

performing morphological expansion on the spine in the segmented image to obtain a morphologically expanded spine image;

transforming the morphologically expanded spine image into a first spine image in the image coordinate system; and acquiring the first spine boundary information corresponding to the first spine image.

3. The single vertebra segmentation method according to claim 1, wherein acquiring first vertebra position information comprises:

constructing a second network model; and acquiring the first vertebra position information from the raw CT image by means of the second network model.

4. The single vertebra segmentation method according to claim 2, wherein acquiring an initial image of the single vertebra according to the first spine boundary information and the first vertebra position information comprises:

determining boundary information of the single vertebra according to the first spine boundary information and the first vertebra position information; and acquiring the initial image of the single vertebra from the first spine image according to the boundary information of the single vertebra.

5. The single vertebra segmentation method according to claim 4, wherein marking the position of the single vertebra in the initial image of the single vertebra to generate an updated image of the single vertebra comprises:

determining second spine boundary information, which is spine boundary information in the initial image of the single vertebra;

updating the position information of the single vertebra in the initial image of the single vertebra according to the second spine boundary information;

acquiring a position marker of the single vertebra in the initial image of the single vertebra according to the updated position information of the single vertebra;

transforming the initial image of the single vertebra containing the position marker of the single vertebra into a position marker image of the single vertebra in a body coordinate system; and generating the updated image of the single vertebra according to the initial image of the single vertebra and the position marker image of the single vertebra.

6. The single vertebra segmentation method according to claim 5, wherein generating the updated image of the single vertebra according to the initial image of the single vertebra and the position marker image of the single vertebra comprises:

constructing a third network model;

transforming the initial image of the single vertebra into an initial image of the single vertebra in the body coordinate system;

inputting the initial image of the single vertebra in the body coordinate system and the position marker image of the single vertebra into the third network model in a preset order;

acquiring an updated image of the single vertebra in the preset order by means of the third network model; and transforming the updated image of the single vertebra into an updated image of the single vertebra in the image coordinate system.

* * * * *